(12) United States Patent
Braga

(10) Patent No.: US 8,419,694 B2
(45) Date of Patent: Apr. 16, 2013

(54) EXTENSION TUBE CLAMPS FOR USE WITH A CATHETER

(75) Inventor: Richard M. Braga, North Easton, MA (US)

(73) Assignee: Covidien LP, Mansfield, MA (US)

( * ) Notice: Subject to any disclaimer, the term of this patent is extended or adjusted under 35 U.S.C. 154(b) by 522 days.

(21) Appl. No.: 12/642,042

(22) Filed: Dec. 18, 2009

(65) Prior Publication Data

US 2010/0168681 A1     Jul. 1, 2010

Related U.S. Application Data

(60) Provisional application No. 61/141,524, filed on Dec. 30, 2008.

(51) Int. Cl.
*A61M 5/00* (2006.01)

(52) U.S. Cl.
USPC ............................. 604/250; 604/32; 604/34

(58) Field of Classification Search ............. 604/250, 604/32, 34
See application file for complete search history.

(56) References Cited

U.S. PATENT DOCUMENTS

| | | |
|---|---|---|
| 1,330,523 A | 2/1920 | Evitts et al. |
| 1,959,074 A | 5/1934 | Bloxsom |
| 2,595,511 A | 5/1952 | Butler |
| 2,844,351 A | 7/1958 | Smith |
| 3,429,549 A | 2/1969 | Swanson |
| 4,248,401 A | 2/1981 | Mittleman |
| 4,292,969 A | 10/1981 | Raible et al. |
| 4,306,705 A | 12/1981 | Svensson |
| 4,307,869 A | 12/1981 | Mittleman |
| 4,434,963 A | 3/1984 | Russell |
| 4,439,179 A | 3/1984 | Lueders et al. |
| 4,560,378 A | 12/1985 | Weiland |
| 4,570,898 A | 2/1986 | Staeubli |
| 4,586,691 A | 5/1986 | Kozlow |
| 4,932,629 A | 6/1990 | Rodomista et al. |
| 4,950,255 A | 8/1990 | Brown et al. |
| 5,035,399 A | 7/1991 | Rantanen-Lee |
| 5,071,411 A | 12/1991 | Hillstead |
| 5,158,553 A | 10/1992 | Berry et al. |

(Continued)

FOREIGN PATENT DOCUMENTS

| | | |
|---|---|---|
| DE | 33 24 699 | 12/1984 |
| DE | 33 24 699 B1 | 12/1984 |

(Continued)

OTHER PUBLICATIONS

European Search Report dated Apr. 9, 2010.

(Continued)

*Primary Examiner* — Kevin C Sirmons
*Assistant Examiner* — Edelmira Bosques
(74) *Attorney, Agent, or Firm* — John Paul Mello, Esq.

(57) ABSTRACT

A clamping assembly includes a first clamping member and a second clamping member. The first clamping member defines a first lumen dimensioned to non-rotatably engage a first portion of a tubular member. Rotating the first clamping member effects a rotation of the first portion of the tubular member. The second clamping member defines a second lumen dimensioned to non-rotatably engage a second portion of the tubular member. Rotating the second clamping member in relation to the first clamping member rotates the second portion of the tubular member in relation to the first portion of the tubular member to twist the tubular member to restrict flow through the tubular member.

10 Claims, 3 Drawing Sheets

U.S. PATENT DOCUMENTS

| | | |
|---|---|---|
| 5,257,770 A | 11/1993 | Grove |
| 5,318,546 A | 6/1994 | Bierman |
| 5,352,214 A | 10/1994 | Oscarsson |
| 5,423,769 A | 6/1995 | Jonkman et al. |
| 5,489,274 A | 2/1996 | Chu et al. |
| 5,853,398 A | 12/1998 | Lal et al. |
| 6,217,564 B1 | 4/2001 | Peters |
| 6,592,558 B2 | 7/2003 | Quah |
| 6,610,027 B1 | 8/2003 | El Hatu |
| 6,689,109 B2 | 2/2004 | Lynn |
| 6,742,760 B2 | 6/2004 | Blickhan et al. |
| 7,011,645 B2 | 3/2006 | McGuckin, Jr. et al. |
| 7,018,374 B2 | 3/2006 | Schon et al. |
| 7,094,218 B2 | 8/2006 | Rome et al. |
| 7,182,746 B2 | 2/2007 | Haarala et al. |
| 7,306,586 B2 | 12/2007 | Beaufore et al. |
| 7,311,697 B2 | 12/2007 | Osborne |
| 7,364,571 B2 | 4/2008 | Schinazi et al. |
| 7,381,204 B2 | 6/2008 | Wilson et al. |
| 2002/0062106 A1 | 5/2002 | Chu et al. |
| 2003/0040724 A1 | 2/2003 | Lynn |
| 2003/0225379 A1 | 12/2003 | Schaffer et al. |
| 2004/0064086 A1 | 4/2004 | Gottlieb et al. |
| 2004/0171997 A1 | 9/2004 | Wilson et al. |
| 2004/0186445 A1 | 9/2004 | Raulerson et al. |
| 2004/0249349 A1 | 12/2004 | Wentling |
| 2005/0256447 A1 | 11/2005 | Richardson et al. |
| 2006/0015074 A1 | 1/2006 | Lynn |
| 2006/0058738 A1 | 3/2006 | Ponzi et al. |
| 2006/0081797 A1 | 4/2006 | Zerfas |
| 2006/0149214 A1 | 7/2006 | Breiter et al. |
| 2006/0189922 A1 | 8/2006 | Amarasinghe et al. |
| 2007/0112313 A1 | 5/2007 | Fangrow |
| 2007/0225682 A1 | 9/2007 | Ash et al. |
| 2007/0255229 A1 | 11/2007 | Kane et al. |
| 2008/0021415 A1 | 1/2008 | Durkin et al. |
| 2008/0029721 A1 | 2/2008 | Miyahara |
| 2008/0051731 A1 | 2/2008 | Schweikert et al. |
| 2008/0082080 A1 | 4/2008 | Braga |
| 2009/0005759 A1 | 1/2009 | Chelak |
| 2009/0030378 A1 | 1/2009 | Garcia |

FOREIGN PATENT DOCUMENTS

| | | |
|---|---|---|
| DE | 9408633 U1 | 10/1994 |
| EP | 1360973 A1 | 11/2003 |
| WO | 97/11296 A1 | 3/1997 |
| WO | WO 97/11296 | 3/1997 |

OTHER PUBLICATIONS

European Search Report for EP 09 18 0739 dated Mar. 29, 2010, 6 pages.

International Search Report dated Jun. 16, 2010 in copending PCT Appln. No. PCT/US2010/030978.

EXTENSION TUBE CLAMPS FOR USE WITH A CATHETER

This application claims priority from U.S. provisional application Ser. No. 61/141,524 filed Dec. 30, 2008, the entirety of which is incorporated herein by reference.

BACKGROUND

1. Technical Field

The present disclosure generally relates to a clamp for obstructing flow through a fluid conduit, and, in particular, relates to clamping assemblies for obstructing fluid flow through extension tubes of a catheter assembly.

2. Description of the Related Art

Catheters are flexible medical instruments which facilitate the withdrawal and introduction of fluids from and to body cavities, ducts, and vessels. Catheter instrumentation may have particular application in a hemodialysis procedure where blood is withdrawn from a blood vessel for treatment, and subsequently returned to the blood vessel for circulation. Known hemodialysis catheters include multiple lumens, such as dual lumen or triple-lumen catheters, which permit bi-directional fluid flow within the catheter whereby one lumen is dedicated for withdrawal of blood from a vessel and the other lumen is dedicated for returning treated blood to the vessel. During an exemplary hemodialysis procedure, a multiple lumen catheter is inserted into a body vessel and blood is withdrawn through an arterial lumen of the catheter. The removed blood is directed to a hemodialysis unit which dialyzes, or purifies, the blood to remove waste and toxins from the blood. The dialyzed blood is returned to the patient through a venous lumen of the catheter.

The use of an extension tube assembly including one or more extension tubes and a clamp for obstructing fluid flow through each extension tube is well known in the art. Typically, the extension tube assembly includes a first extension tube which fluidly connects the venous lumen of the catheter to the hemodialysis unit and a second extension tube which fluidly connects the arterial lumen of the catheter to the hemodialysis unit. A clamp is positioned about each extension tube to facilitate control of fluid through each extension tube.

Chronic hemodialysis catheters are positioned within a patient for long term use and, thus may remain in a patient for extended periods of time. Repeated use of the clamp to control flow of fluid through a respective extension tube can cause the extension tube to wear such that replacement of the extension tube and/or the catheter is required. In addition, because chronic catheters are positioned for long term use, a non-ergonomically configured clamp can cause discomfort to the patient.

Accordingly, a continuing need exists in the art for an extension tube assembly which includes a clamp or clamps which minimize wear and tear on the extension tube of the extension tube assembly, minimize discomfort to a patient, and are easy to operate.

SUMMARY

The present disclosure relates to a clamping assembly including a first clamping member and a second clamping member. The first clamping member defines a first lumen dimensioned to non-rotatably engage a first portion of a tubular member. Rotating the first clamping member effects a rotation of the first portion of the tubular member. The second clamping member defines a second lumen dimensioned to non-rotatably engage a second portion of the tubular member. Rotating the second clamping member in relation to the first clamping member rotates the second portion of the tubular member in relation to the first portion of the tubular member to twist the tubular member to restrict flow through the tubular member.

In one embodiment, the first clamping member defines a first contoured surface and the second clamping member defines a second contoured surface. The first and second contoured surfaces are complementary to each other. In addition, the first and second contoured surfaces are configured to releasably engage each other in at least two orientations to prevent relative rotation of the first clamping member in relation to the second clamping member.

In one embodiment, the first and second contoured surfaces face each other.

In one embodiment, the first contoured surface has a wave configuration around a circumference thereof.

In one embodiment, the second contoured surface has a wave configuration around a circumference thereof.

In one embodiment, the first and second clamping members include indicia for indicating the orientation of the first and second clamping member relative to the each other.

In one embodiment, the entire indicia can be read from one side when the tubular member is twisted.

In one embodiment, at least one of the first and second clamping members includes a recess for facilitating gripping.

In one embodiment, the tubular member is made of an elastomeric material.

The present disclosure further relates to a catheter assembly including an extension tube defining a bore, a first clamping member defining a first lumen, and a second clamping member defining a second lumen. The extension tube has first and second portions. The first lumen is dimensioned to non-rotatably engage the first portion of the extension tube. In use, rotating the first clamping member effects rotation of the first portion of the extension tube. The second lumen is dimensioned to non-rotatably engage the second portion of the extension tube. In use, rotating the second clamping member in relation to the first clamping member rotates the second portion of the extension tube in relation to the first portion of the extension tube to twist the extension tube to restrict flow through the extension tube.

In one embodiment, the first clamping member defines a first contoured surface and the second clamping member defines a second contoured surface. The first and second contoured surfaces are complementary to each other. In addition, the first and second contoured surfaces are configured to releasably engage each other in at least two orientations to prevent relative rotation of the first clamping member in relation to the second clamping member.

In one embodiment, the first and second contoured surfaces face each other.

In one embodiment, the first contoured surface has a wave configuration around a circumference thereof.

In one embodiment, the second contoured surface has a wave configuration around a circumference thereof.

In one embodiment, the first and second clamping members include indicia for indicating the orientation of the first and second clamping member relative to the each other.

In one embodiment, the entire indicia can be read from one side when the tubular member is twisted.

In one embodiment, at least one of the first and second clamping members includes a recess for facilitating gripping.

In one embodiment, the tubular member is made of an elastomeric material.

BRIEF DESCRIPTION OF THE DRAWINGS

Various embodiments of the presently disclosed clamp assembly are described herein with references to the accompanying drawings, wherein.

DETAILED DESCRIPTION OF THE EMBODIMENTS

In the discussion that follows, the term "proximal" or "trailing" will refer to the portion of a structure that is closer to a clinician, while the term "distal" or "leading" will refer to the portion that is farther from the clinician. As used herein, the term "subject" refers to a human patient or other animal. The term "clinician" refers to a doctor, nurse or other care provider and may include support personnel.

Figure 1:
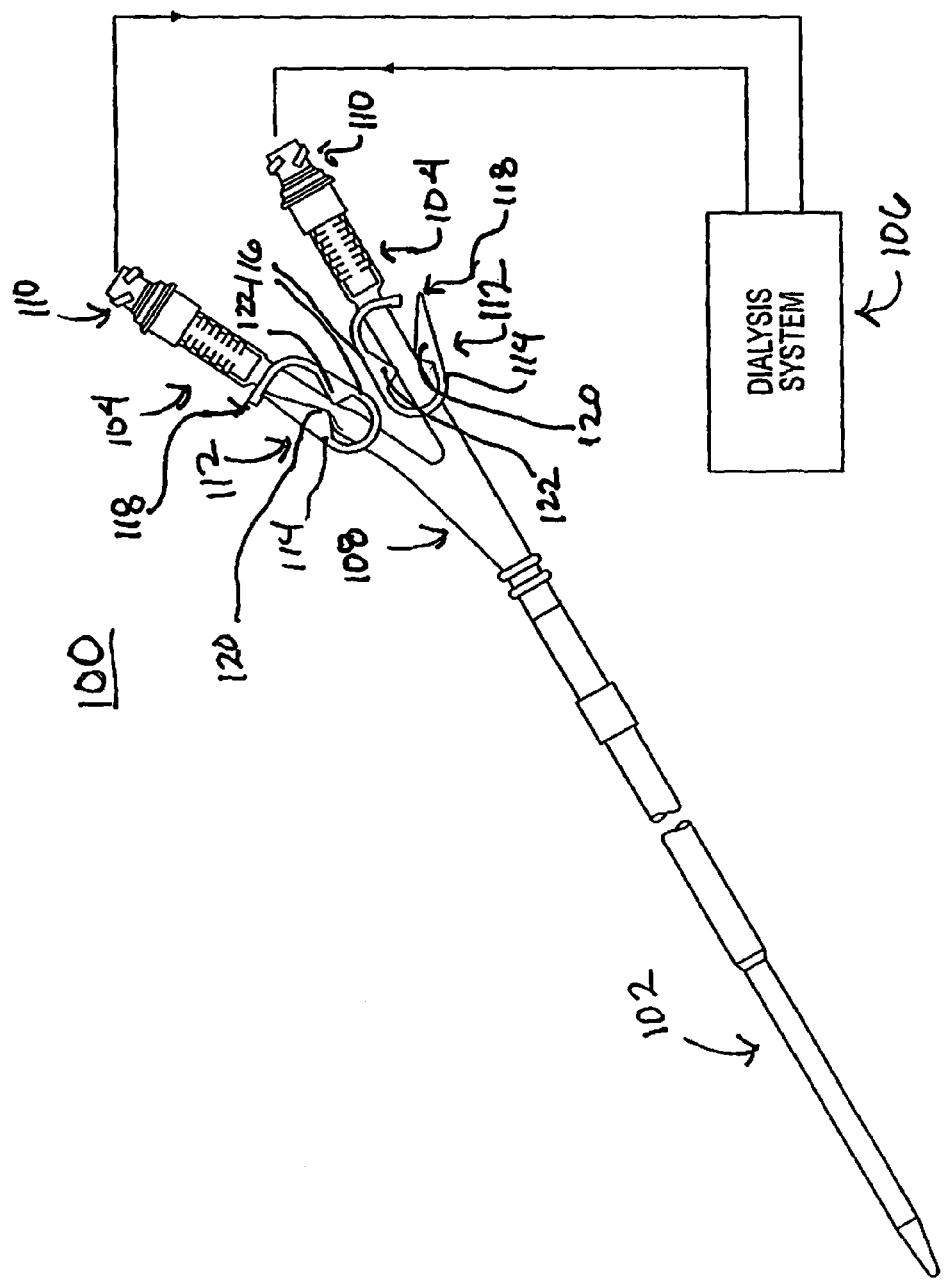
FIG. 1 labeled "Prior Art" is a side plan view of a conventional catheter assembly operatively connected to a dialysis system and incorporating a conventional extension tube clamp.

The presently disclosed clamping assembly may be employed with dialysis catheter systems. A conventional dialysis catheter assembly 100 is shown in FIG. 1. Catheter assembly 100 includes a catheter 102, extension tubes 104, and a hub or housing 108 fluidly interconnecting catheter 102 and extension tubes 104. Typically, extension tubes 104 are in fluid communication with a dialysis system 106. Each extension tube 104 may include a luer fitting 110 attached to a proximal end thereof to facilitate fluid connection between catheter assembly 100 and dialysis system 106.

Catheter assembly 100 additionally includes a pair of clamps 112 operatively associated with each extension tube 104. Each clamp 112 is configured to compress an extension tube 104, thereby obstructing or at least hindering fluid flow through the extension tube 104. Each clamp 112 includes first and second elongate portions 114, 116 and a snap-fit lock 118 which is adapted to maintain the relative position of first and second elongate portions 114, 116. Each of first and second elongate portions 114, 116 includes opposed compression segments 120, 122 which jointly compress an extension tube 104 when first and second elongate portions 114, 116 are moved toward each other. First and second elongate portions 114, 116 are normally biased away from each other. As shown in FIG. 1, clamps 112 allow clinicians to clamp one extension tube 104, while maintaining fluid flow through the other extension tube 104 or to clamp both extension tubes 104 simultaneously.

Figure 2:
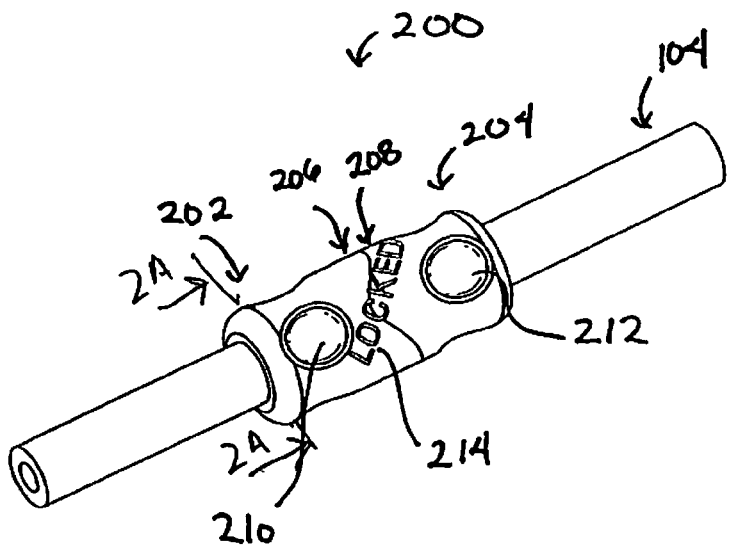
FIG. 2 is perspective view of a clamp for an extension tube in accordance with an embodiment of the present disclosure and in a locked position.
Figure 3:
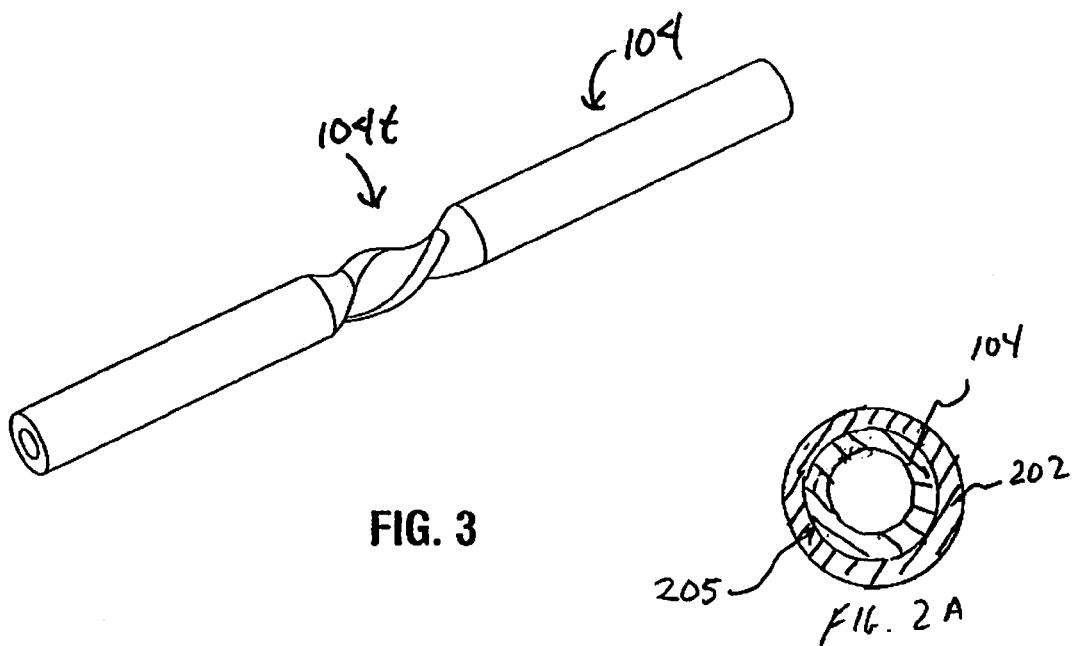
FIG. 3 is a perspective view of an extension tube with the clamp removed illustrating a twisted condition of the extension tube with the clamp in the locked position of FIG. 2.
Figure 2A:
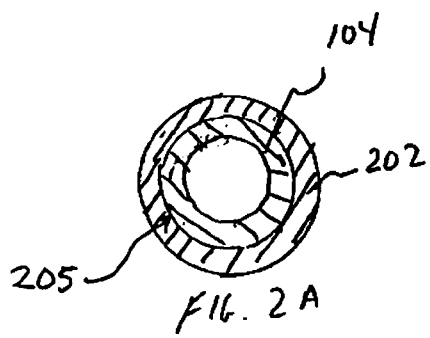
FIG. 2A is a front cross-sectional view of the clamp and the extension tube of FIG. 2, taken along section line 2-2 of FIG. 2.

FIGS. 2-5 illustrate one embodiment of a clamping assembly 200 in accordance with the principles of the present disclosure. Clamping assembly 200 includes a first clamping member or section 202 and a second clamping member or section 204. Each of the first and second clamping sections 202, 204 includes inner surfaces (not shown) defining a longitudinal lumen 205 (FIG. 2A) extending therethrough. The longitudinal lumens 205 of first and second clamping sections 202, 204 are dimensioned to receive extension tube 104. In one embodiment, extension tube 104 can slide longitudinally through longitudinal lumens 205 of first and second clamping sections 202, 204 but is incapable of rotating within the longitudinal lumens 205. Alternatively, clamping sections 202, 204 may be longitudinally fixed with respect to extension tubes 202, 204. Longitudinal lumens 205 of first and second clamping sections 202, 204 are dimensioned to prevent relative rotation of extension tube 104 in relation to a respective clamping section 202 or 204 when either first or second clamping sections 202, 204 are rotated. In one embodiment, the inner surfaces of first and second clamping sections 202, 204 frictionally engage the outer surface of extension tube 104 in a manner to prevent relative rotation of extension tube 104 and a respective clamping section 202, 204. Alternatively, other structure or means may be provided to prevent rotation of clamping section 202 and/or 204 in relation to extension tube 104, e.g., interlocking structure, adhesives, etc. Accordingly, rotation of first and second clamping sections 202, 204 causes corresponding rotation of the respective extension tube 104. As such, relative rotation of clamping section 202 with respect to clamping section 204 forms a twist or kink in extension tube 104 as depicted in FIGS. 2-3. To facilitate the formation of a kink on extension tube 104 during rotation of first clamping member 202 in relation to second clamping section 204, an elastomer or any other suitable flexible material may be employed to make extension tube 104. In one embodiment, the flexible material can be stretched to facilitate axial separation of first and second clamping sections 202 and 204.

In one embodiment, first clamping section 202 defines a first contoured surface 206 and second clamping section 204 defines a second contoured surface 208. First contoured surface 206 is complementary to the second contoured surface 208. When clamping assembly 200 is placed around extension tube 104, first and second contoured surfaces 206, 208 face each other. The clinician can adjust the relative orientation of first and second clamping sections 202, 204. By adjusting the relative orientation of first and second clamping sections 202, 204, the clinician can also adjust the relative orientation of first and second contoured surfaces 206, 208. First contoured surface 206 is adapted to engage or interlock with second contoured surface 208 in at least two orientations to retain clamping sections 202 and 204 in one of two fixed positions in relation to the other. The relative orientation of the clamping sections 202 and 204, and thus, the relative orientation of the first and second contoured surfaces 206, 208 controls whether or not a kink is formed in a respective extension tube 104. When first and second contoured surfaces 206, 208 are engaged to each other, first and second clamping sections 202, 204 are inhibited from rotating in relation to each other. Although the depicted embodiment illustrates contoured surfaces 206, 208, clamping assembly 200 may alternatively include other configurations, means, mechanism, or devices to effect engagement between the first and second clamping sections 202 and 204, e.g., ball and detents.

The relative orientation of first and second clamping members 202 and 204 controls whether clamping assembly 200 allows or inhibits fluid flow through extension tube 104. More specifically, when clamping section 202 is rotated in relation to clamping section 204 to a "locked position" to form a kink in extension tube 104, fluid flow through extension tube 104 is inhibited. When clamping section 202 is rotated in relation to clamping section 204 to an "unlocked position" to remove a kink from extension tube 104, fluid is free to flow through extension tube 104.

To move catheter assembly 200 between locked and unlocked positions, the clinician separates first and second clamping sections 202, 204 by pulling clamping section 202 and 204 apart, and then rotating first and second clamping sections 202, 204 relative to each other until contoured surfaces 206, 208 reach an orientation where they can interlock with one another. First and second clamping sections 202, 204 may each include gripping recesses 210, 212 adapted to receive the clinician's fingers. Recesses 210, 212 facilitate the rotation of first and second clamping sections 202, 204. In one embodiment, catheter assembly 200 may include indicia 214 to indicate to the clinician whether clamping assembly 200 is located in the locked position or in the unlocked position. In the embodiment depicted in FIG. 2, indicia 214 is oriented or positioned to spell the word "locked" when the first and second clamping sections 202, 204 are in the locked position. The indicia 214, e.g., the word "locked", can only be read in its entirety when clamping sections 202 and 204 are positioned to inhibit flow through extension tube 104.

Figure 4:
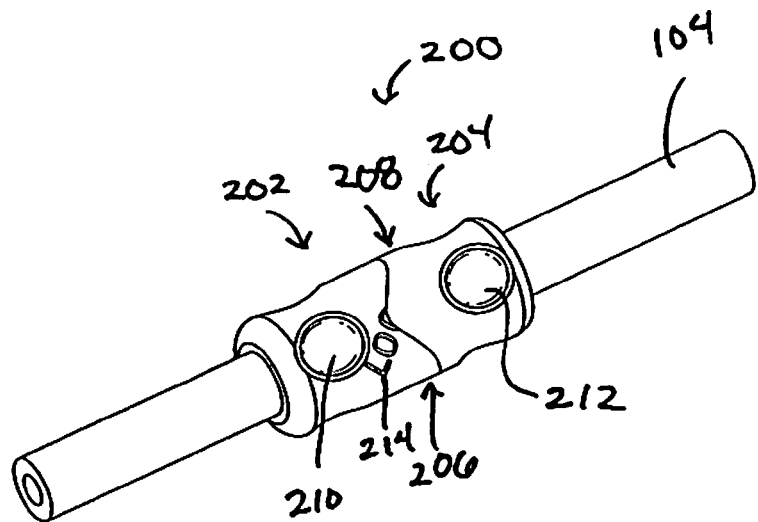
FIG. 4 is a perspective view of the clamp of FIG. 2 in an unlocked position.

During operation, clamping assembly 200 controls the flow passing through extension tube 104. To allow fluids to freely flow through extension tube 104, the clinician places catheter assembly 200 in the unlocked position, as illustrated in FIG. 4. While catheter assembly 200 is in the unlocked position, the portions of the extension tube 104 positioned within the longitudinal lumens of first and second clamping sections 202, 204 are not twisted or kinked and only a portion of indicia 214 is readily visible to the clinician from one side of the assembly 200. Since extension tube 104 is not twisted, fluid is able to flow through extension tube 104. First contoured surface 206 interlocks with or engages second contoured surface 208 when clamping assembly 200 is oriented in the unlocked position. Engagement of first and second contoured surfaces 206, 208 inhibits first and second clamping sections 202, 204 from rotating in relation to each other from the unlocked position to the locked position.

Figure 5:
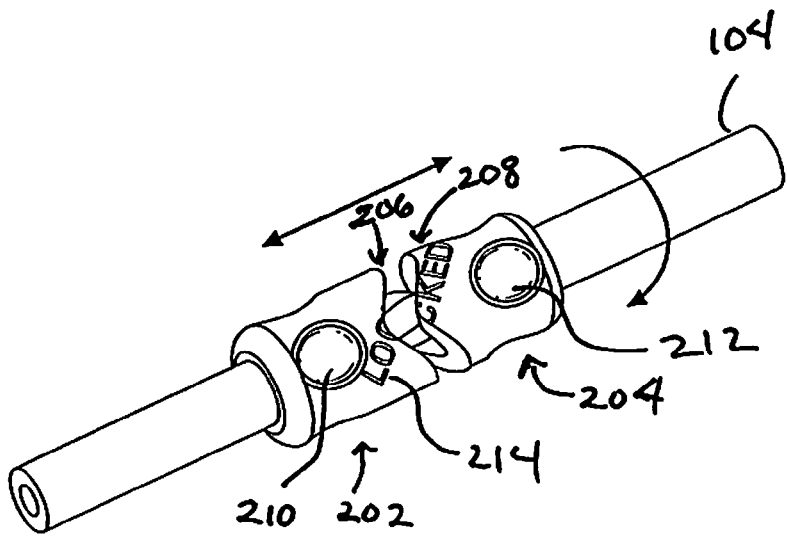
FIG. 5 is a perspective view of the clamp of FIG. 2 being rotated toward the locked position.

Clamping assembly 200 can also restrict the passage of fluid through extension tube 104 when placed in the locked position. The clinician places clamping assembly 200 in the locked position by initially separating first and second clamping sections 202, 204, as shown in FIG. 5. When the clinician moves first and second clamping sections 202, 204 away from each other, first contoured surface 206 disengages from second contoured surface 208. Once first and second contoured surfaces 206, 208 are separated, first and second clamping sections 202, 204 are able to rotate in relation to each other. After separating first and second clamping sections 202, 204, the clinician rotates first and second clamping sections 202, 204 relative to each other until contoured surfaces 206, 208 are positioned in an orientation where they can once again engage one another, e.g., about 180°, 540° or greater. As first and second clamping sections 202, 204 rotate relative to each other, the inner surfaces of first and second clamping sections 202, 204 engage the outer periphery of portions of the extension tube 104 located inside the longitudinal lumens of first and second clamping sections 202, 204 to twist extension tube 104 as seen in FIG. 3. The twisted portion 104t of extension tube 104 obstructs the passage of fluid through extension tube 104. After twisting extension tube 104, the clinician optionally slides first and second clamping sections 202, 204 toward each other to engage contoured surfaces 206, 208. Alternatively, the flexibility of extension tubes 104 may automatically return clamping sections 202, 204 to an engaged position. Engagement of contoured surface 206 with contoured surface 208 prevents rotation of first and second clamping sections 202, 204 from the locked position. Once clamping assembly 200 is placed in the locked position, the indicia 214, e.g., "locked", is fully visible, as seen in FIG. 2.

It will be understood that various modifications may be made to the embodiments of the presently disclosed clamping assemblies. For instance, the presently disclosed clamping assemblies may clamp any conduit capable of transferring fluid from one point to another. Additionally, the indicia 214 may be located on extension tube 104 and visible to the clinician when the clinician moves first and second clamping sections 202, 204 away from each other. The orientation or position of indicia 214 along twisted portion 104t of extension tube 104 informs the clinician as to whether flow is inhibited through extension tube 104. Therefore, the above description should not be construed as limiting, but merely as exemplifications of embodiments. Those skilled in the art will envision other modifications within the scope and spirit of the present disclosure.

What is claimed is:

1. A clamping assembly, comprising: a first clamping member defining a first lumen dimensioned to non-rotatably engage a first portion of a tubular member, wherein rotating the first clamping member effects rotation of the first portion of the tubular member; and a second clamping member defining a second lumen dimensioned to non-rotatably engage a second portion of the tubular member, wherein rotating the second clamping member in relation to the first clamping member rotates the second portion of the tubular member in relation to the first portion of the tubular member to twist the tubular member to restrict flow through the tubular member;

wherein the first clamping member defines a first contoured surface and the second clamping member defines a second contoured surface, the first and second contoured surfaces facing each other and being complementary to each other, the first and second contoured surfaces each having a wave configuration around a circumference thereof, whereby the first and second contoured surfaces are configured to releasably engage each other in at least two orientations of the clamping assembly to prevent relative rotation of the first clamping member in relation to the second clamping member, the first and second contoured surfaces being interlocked in the at least two orientations.

2. The clamping assembly of claim 1, wherein the first and second clamping members include indicia for indicating the relative orientation of the first clamping member and second clamping member relative to each other.

3. The clamping assembly of claim 2, wherein the entire indicia can be read from one side of the clamping assembly when the tubular member is twisted.

4. The clamping assembly of claim 1, wherein at least one of the first and second clamping members includes a recess for facilitating gripping.

5. The clamping assembly of claim 1, wherein the tubular member is made of an elastomeric material.

6. A catheter assembly, comprising: an extension tube defining a bore, the extension tube having first and second portions; a first clamping member defining a first lumen dimensioned to non-rotatably engage the first portion of the extension tube, wherein rotating the first clamping member effects rotation of the first portion of the extension tube; and a second clamping member defining a second lumen dimensioned to non-rotatably engage the second portion of the extension tube, wherein rotating the second clamping member in relation to the first clamping member rotates the second portion of the extension tube in relation to the first portion of the extension tube to twist the extension tube to restrict flow through the extension tube;

wherein the first clamping member defines a first contoured surface and the second clamping member defines a second contoured surface, the first and second contoured surfaces facing each other and being complementary to each other, the first and second contoured surfaces each having a wave configuration around a circumference thereof, whereby the first and second contoured surfaces are configured to releasably engage each other in at least two orientations to prevent relative rotation of the first clamping member in relation to the second clamping member, the first and second contoured surfaces being interlocked in the at least two orientations.

7. The catheter assembly of claim 6, wherein the first and second clamping members include indicia for indicating the relative orientation of the first clamping member and second clamping member.

8. The catheter assembly of claim 7, wherein the indicia is positioned on the first and second clamping members to be read from one side of the clamp assembly when the extension tube is twisted.

9. The catheter assembly of claim 6, wherein at least one of the first and second clamping members includes a recess for facilitating gripping.

10. The catheter assembly of claim 6, wherein the tubular member is made of an elastomeric material.

* * * * *